(12) United States Patent
Sunohara et al.

(10) Patent No.: US 7,017,948 B2
(45) Date of Patent: Mar. 28, 2006

(54) DIALYZER CONNECTING COUPLER

(75) Inventors: Takashi Sunohara, Osaka (JP); Yasuhiko Morita, Osaka (JP); Masuda Toshiaki, Osaka (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 10/869,043

(22) Filed: Jun. 17, 2004

(65) Prior Publication Data

US 2004/0262917 A1    Dec. 30, 2004

(30) Foreign Application Priority Data

Jun. 18, 2003    (JP) .............................. 2003-174029

(51) Int. Cl.
*F16L 33/00* (2006.01)
(52) U.S. Cl. .................. 285/244; 285/277; 285/239
(58) Field of Classification Search ................ 285/276, 285/277, 403, 244, 107, 109, 239
See application file for complete search history.

(56) References Cited

U.S. PATENT DOCUMENTS

| | | | | |
|---|---|---|---|---|
| 2,518,542 A | * | 8/1950 | Hansen | 285/277 |
| 2,631,872 A | * | 3/1953 | Wurmser | 285/277 |
| 3,334,860 A | * | 8/1967 | Bolton, Jr. | 251/149.1 |
| 4,198,080 A | * | 4/1980 | Carpenter | 285/277 |
| 4,496,458 A | * | 1/1985 | Lee | 210/90 |
| 5,052,725 A | * | 10/1991 | Meyer et al. | 285/308 |
| 5,813,703 A | * | 9/1998 | Reinholz | 285/179 |
| 6,517,124 B1 | * | 2/2003 | Le Quere | 285/340 |
| 2005/0006297 A1 | * | 1/2005 | Moriwaki et al. | 210/321.6 |

FOREIGN PATENT DOCUMENTS

| | | |
|---|---|---|
| DE | 85 19 806 U1 | 8/1985 |
| JP | 9-51945 * | 2/1997 |
| JP | 2758148 B1 | 3/1998 |
| JP | 1170163 * | 3/1999 |
| JP | 2000-14772 A | 1/2000 |
| JP | 2001-299907 * | 10/2001 |

* cited by examiner

*Primary Examiner*—David Bochna
(74) *Attorney, Agent, or Firm*—Kubovcik & Kubovcik

(57) ABSTRACT

A connecting coupler which reduces the risk that an endotoxin or the like enters a dialysis solution and that the connecting coupler itself is deformed including a body made of an elastic material in which a tip portion of a connection plug of a dialyzer can be removably fitted into a plug-receiving opening portion of a solution transferring passage inside the body; a line connector which is fitted into the body and communicates with the solution transferring passage; a coupling tube which has a fixing portion fixedly fitted on the tip portion of the body and a coupling portion projecting from the fixing portion toward a front in an axial direction and removably fitable onto the connection plug; and a fixing mechanism which releasably fixes the coupling tube to the connection plug.

2 Claims, 3 Drawing Sheets

Prior Art

DIALYZER CONNECTING COUPLER

TECHNICAL FIELD OF THE INVENTION

The present invention relates to a dialyzer connecting coupler for connecting a solution transferring line such as a dialysis solution circulating hose to a connection plug (a dialysis solution inlet or outlet) of a dialyzer.

BACKGROUND OF THE INVENTION

A dialyzer connecting coupler which connects a solution transferring line such as a dialysis solution circulating hose to a connection coupler of a dialyzer is shown in FIG. 3 by way of example. In this dialyzer, a fitting portion 32 into which a connection plug is to be removably fitted and a cavity portion 33 for communicating with the inside of the connection plug are formed in the inside of a body 31, and a tube-shaped, hose connecting portion 34 is formed integrally with the body 31 in a laterally projecting shape, and its inside communicates with the cavity portion 33. In addition, an O-ring 35 for liquid-tightly connecting the connection plug and the fitting portion 32 is provided in the body 31, and the body 31 is provided with a fixing mechanism 36 which releasably fixes the connection plug to the body 31.

In recent years, in view of greater improvements in substance permeation performance of dialyzers due to higher performance thereof, more attention has been drawn to the risk that a pyrogenic substance such as an endotoxin will enter into blood from a dialysis solution. From this possibility, the necessity to purify dialysis solutions has increased, and various contrivances have been made. For example, during actual production of a dialysis solution, RO water (water processed by a reverse osmosis film) is used, and during dialysis, an endotoxin removing filter is disposed in front of the dialyzer.

SUMMARY OF THE INVENTION

However, even if a dialysis solution is fully purified as mentioned above, in the case where the connecting coupler shown in FIG. 3 is used as a connecting coupler which is connected to a connection plug of a dialyzer, as mentioned above, there is a risk that bacteria are generated in the connecting coupler and endotoxin separates from the bacteria and enters into the dialysis solution. The main cause of this risk is that when the connection plug and the connecting coupler are connected to each other, a dead space (gap) is formed in a portion surrounding the O-ring 35 and the dialysis solution stays in this portion and, after the completion of dialysis, the portion surrounding the O-ring 35 is difficult to clean.

The present invention aims to provide a dialyzer connecting coupler capable of solving the above-mentioned problem.

To achieve the above object, the invention is characterized by including:

A) a body which is formed of an elastic material and has a solution transferring passage formed in its inside, the solution transferring passage having a plug-receiving opening portion opened at a tip portion thereof, a tip portion of a connection plug of a dialyzer being capable of being removably fitted into this plug-receiving opening portion;

B) a line connector which is fitted into the body so that its inside communicates with the solution transferring passage, and to which a solution transferring line is connected;

C) a coupling tube which is formed in a tubular shape and has a fixing portion fixedly fitted on the tip portion of the body and a coupling portion projecting from the fixing portion toward a front in an axial direction and removably fitted onto a portion of the connection plug that excludes the tip portion thereof; and D) a fixing mechanism which releasably fixes the coupling tube to the connection plug in the state of pressing the body against the connection plug, the plug-receiving opening portion being made larger in diameter than the portion of the solution transferring passage that neighbors the plug-receiving opening portion, an inside bottom of the plug-receiving opening portion forming a first seal surface which, when the connection plug is connected, is brought into abutment with the connection plug and is elastically deformed toward a base portion of the body to come into liquid-tight contact with a tip face of the connection plug, a side surface of the plug-receiving opening portion forming a second seal surface which is flush with and contiguous to an inside surface of the coupling portion of the coupling tube and, when the connection plug is connected, is brought into abutment with the connection plug and is elastically deformed diametrically outwardly to come into liquid-tight contact with the side surface of the tip portion of the connection plug.

It is to be noted that the fixing mechanism is also formed of a metal material.

DETAILED DESCRIPTION OF THE INVENTION

Figure 1:
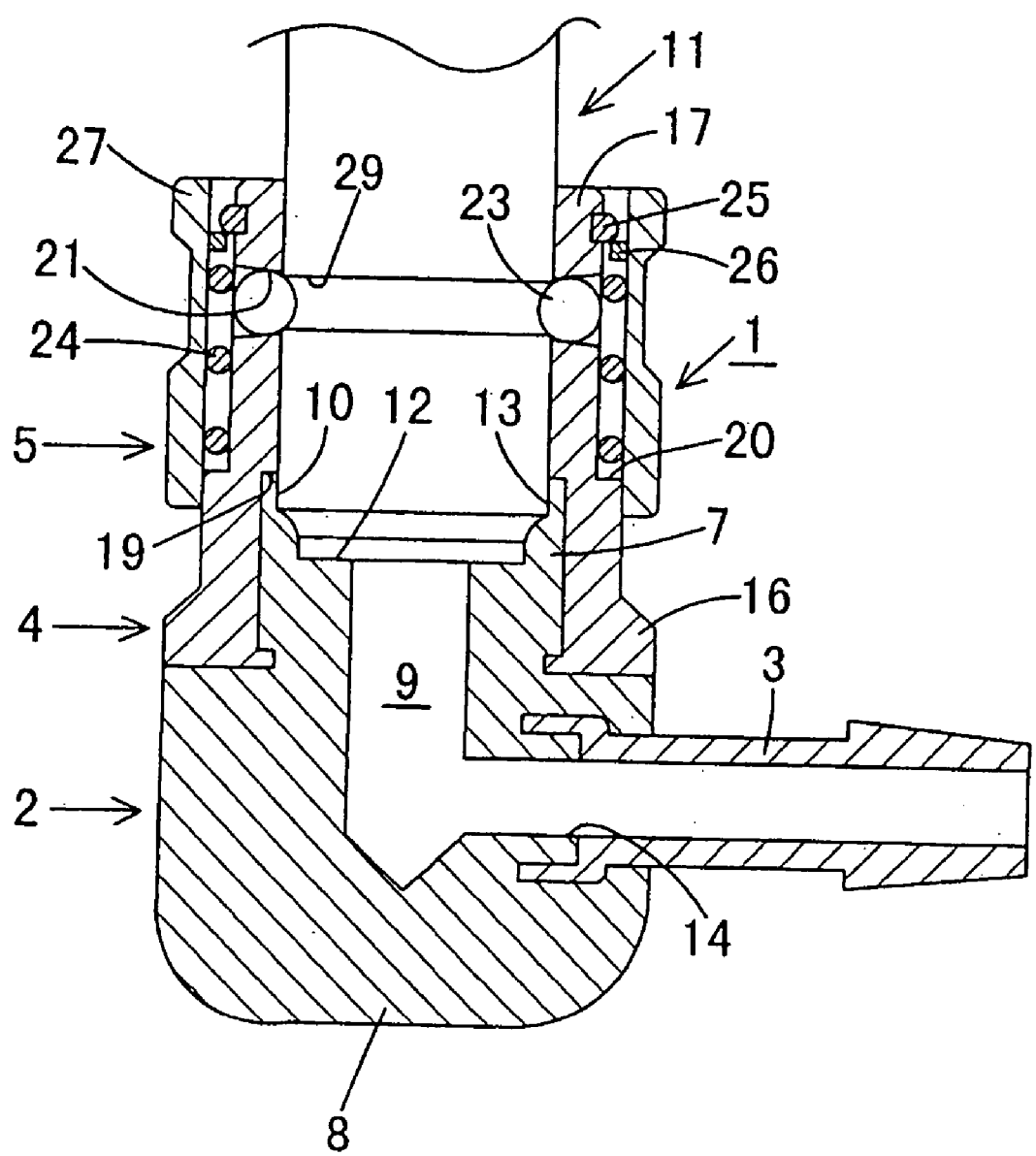
[FIG. 1] A cross-sectional view showing the operating state of the connector of the invention.

One embodiment of the invention is described below with reference to FIGS. 1 and 2. A dialyzer connecting coupler 1 has a body 2, a line connector 3, a coupling tube 4, a fixing mechanism 5, and the like.

The body 2 is integrally formed, and a tip portion 7 is made smaller in diameter than a base portion 8 and an L-shaped solution transferring passage 9 is formed in the inside. One end portion of the solution transferring passage 9 has a plug-receiving opening portion 10 which is opened in a tip surface of the body 2, and a connection plug 11 of a dialyzer (not shown) is removably relatively fitted into the opening portion 10. The plug-receiving opening portion 10 is made larger in diameter than the portion of the solution transferring passage 9 that neighbors the plug-receiving opening portion 10, and the inside bottom of the plug-receiving opening portion 10 forms a first seal surface 12, and the side surface of the plug-receiving opening portion 10 forms a second seal surface 13. The first seal surface 12, when the connection plug 11 is connected, abuts with the connection plug 11 (is pressed by the connection plug 11) and is elastically deformed toward the base portion 8 of the body 2 and establishes liquid-tight contact with the tip face of the connection plug 11. When the connection plug 11 is unconnected, the second seal surface 13 assumes the state shown in FIG. 2, whereas when the connection plug 11 is connected, the second seal surface 13, as shown in FIG. 1, abuts with the connection plug 11 and the whole (or approximately the whole, an essential portion, or a part) of the second seal surface 13 is elastically deformed diametrically outwardly and establishes liquid-tight contact with the side surface of the tip portion of the connection plug 11. The other end portion of the solution transferring passage 9 forms a line-receiving opening portion 14 which is opened on one side. Incidentally, the line-receiving opening portion 14 may also be opened on another side such as the base end face of the body 2.

The body 2 is formed of an elastic material (i.e., a rubber-like elastic material or a rubber-like elastomer). As this elastic material, a material is used which is low in elastic modulus and is large in elastic limit and which does not physically nor chemically react with dialysis solutions (namely, is inactive against dialysis solutions) and can prevent penetration of microorganisms. Specifically, silicone rubber and various other elastomers are preferred.

The line connector 3 is integrally formed in a tubular shape, and its base portion is fixedly inserted in a side portion of the base portion 8 of the body 2 and its interior communicates with the line-receiving opening portion 14. Incidentally, the mounting of the line connector 3 on the body may be effected by insert-molding, or the line connector 3 may be inserted into the body 2 and fixed thereto with an adhesive. A solution transferring line (not shown) such as a dialysis solution circulating hose is separably fitted onto and connected to the tip portion of the line connector 3. The line connector 3 is formed of a metal material or a synthetic resin material. As this metal material, a material is used which does not physically nor chemically react with dialysis solutions (namely, is inactive against dialysis solutions) and can prevent penetration of microorganisms. Specifically, stainless steel is preferred. As the synthetic resin, synthetic resins for medical use can be used.

The coupling tube 4 is integrally formed in a cylindrical shape, and has a fixing portion 16 and a coupling portion 17. The fixing portion 16 is fixedly fitted on the tip portion 7 of the body 2. Incidentally, the mounting of the coupling tube 4 on the body 2 may be effected by insert-molding, or the fixing portion 16 may be fitted onto the body 2 and fixed thereto with an adhesive. The coupling portion 17 is adapted to be removably fitted onto the portion of the connection plug 11 that excludes the tip portion thereof, and projects from the fixing portion 16 toward the front in the axial direction. The outside and inside diameters of the coupling portion 17 are made smaller than those of the fixing portion 16, and a stepped surface 19 which has a planar shape facing toward the base portion of the body 2 is formed on an inside surface of the boundary portion between the fixing portion 16 and the coupling portion 17, and this stepped surface 19 is in close contact with the entire tip surface of the body 2. A stepped surface 20 which has a planar shape facing toward the base portion of the body 2 is formed on an outside surface of the boundary portion between the fixing portion 16 and the coupling portion 17. In addition, the inside surface of the coupling portion 17 is made flush with and contiguous with the second seal surface 13, and a plurality of ball holes 21 each having a tapered shape extending through the coupling portion 17 in a radial direction thereof are formed in a portion of the coupling portion 17 that is near the tip thereof, in such a manner as to be circumferentially spaced apart from one another at equal intervals. The coupling tube 4 is formed of a metal material or a synthetic resin material. As the metal material, a material similar to that of the line connector 3 is used.

The fixing mechanism 5 releasably fixes the coupling tube 4 to the connection plug 11 in a state of the body 2 pressing against the connection plug 11, and includes a plurality of balls 23, a coil spring 24, first and second ring-shaped stoppers 25 and 26, a sleeve 27 and the like. Each of the members of the fixing mechanism 5 is formed of a metal material or a synthetic resin material. As the metal material, a material similar to that of the line connector 3 is used.

The balls 23 are provided in the respective ball holes 21 of the coupling tube 4 so that the respective balls 23 can move in a radial direction of the coupling tube 4. As shown in FIG. 1, each of the balls 23 is positionally changeable between an engagement position where the ball 23 projects into the inside of the coupling tube 4 and disengageably engages with a peripheral groove 29 of the connection plug 11 and an allowable position which is a position radially outward of the engagement position with respect to the radial direction of the coupling tube 4 and allows the connection plug 11 to be fitted into and removed from the coupling tube 4.

The coil spring 24 is fitted on the coupling portion 17 of the coupling tube 4 and the balls 23.

The first stopper 25 is fitted on the peripheral surface of the coupling portion 17 of the coupling tube 4 on the side of the balls 23 which is close to the tip of the coupling portion 17, and the second stopper 26 is fitted in the sleeve 27 on the side of the tip thereof and is positioned closer to the body 2 than is the first stopper 25. The coil spring 24 is resiliently inserted between the stepped surface 20 of the coupling tube 4 and the second stopper.

The sleeve 27 is axially movably fitted on the coupling tube 4 and the coil spring 24, and is urged toward the front (upward in FIG. 1) in the axial direction by the coil spring 24. The sleeve 27, as shown in FIG. 1, is positionally changeable via the coil spring 24 between a fixing position for holding the balls 23 at the engagement position and a release position. When the sleeve 27 is at the release position, the sleeve 27 is located on a side which is axially closer to the body 2 than when the sleeve 27 is at the holding position, and compresses the coil spring 24 toward the body 2 beyond the balls 23 in the axial direction to allow the balls 23 to move to the allowable position.

Figure 2:
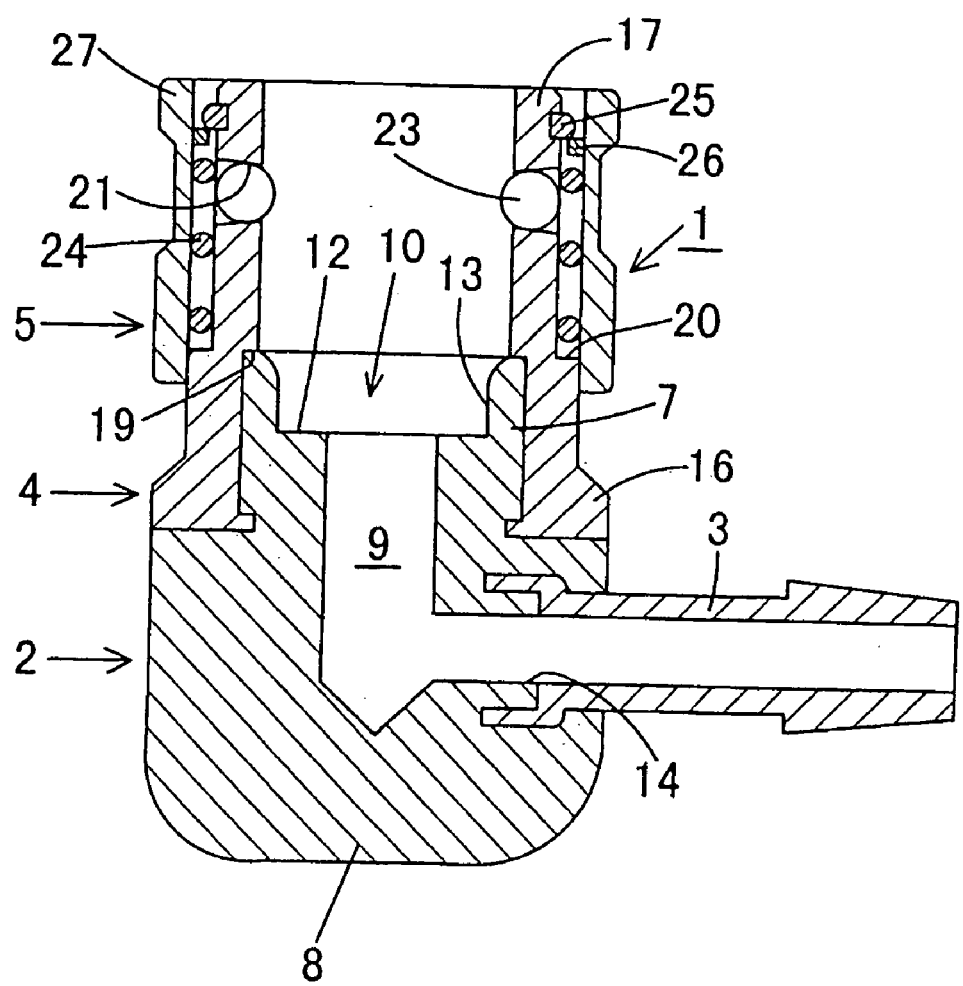
[FIG. 2] A cross-sectional view of one embodiment of the invention.
Figure 3:
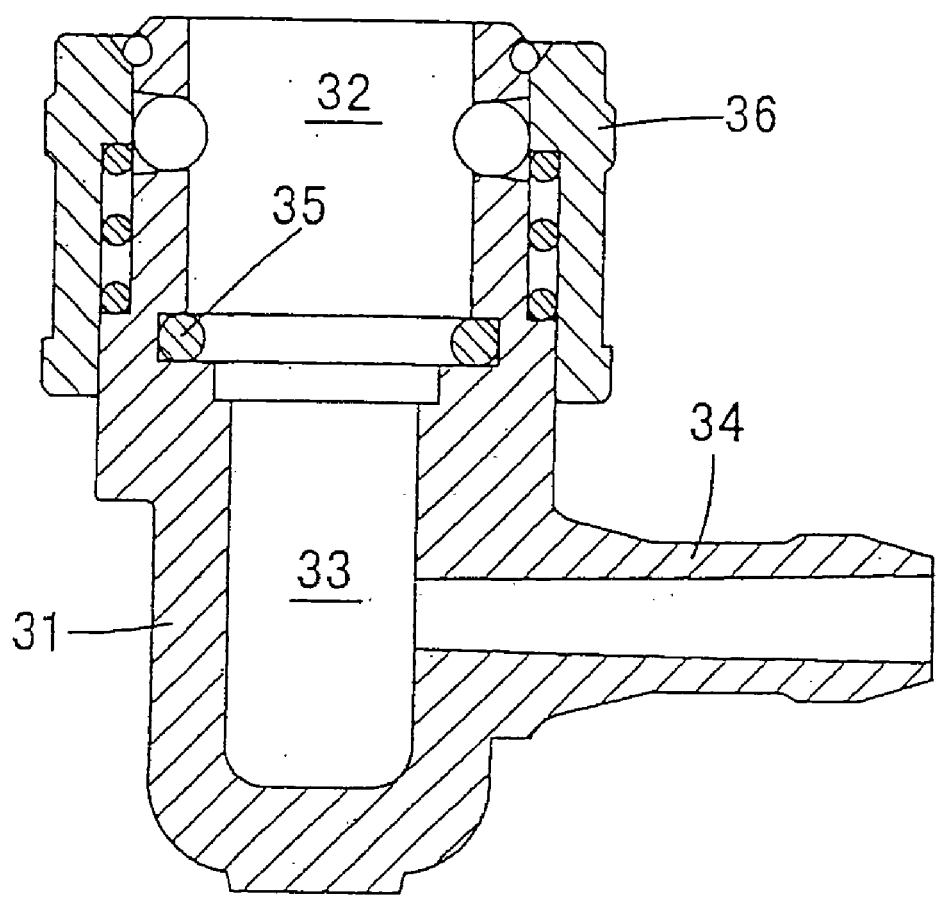
[FIG. 3] A cross-sectional view showing a prior-art example.

According to the above-described construction example, the dialyzer connecting coupler 1, when not connected to the connection plug 11 of the dialyzer, is in the state shown in FIG. 2. During dialysis, a dialysis solution circulating hose is connected to the line connector 3 of the dialyzer connecting coupler 1, and as shown in FIG. 1, the dialyzer connecting coupler 1 is connected to the connection plug 11 of the dialyzer.

At the time of dialysis, the sleeve 27 of the fixing mechanism 5 is pressed against the coil spring 24 toward the body 2 and is set to the release position, and in this state, the connection plug 11 is fitted into the coupling portion 17 of the coupling tube 4 and the plug-receiving opening portion 10 of the body 2. At this time, since the balls 23 move to the allowable position, the connection plug 11 can be fitted into the plug-receiving opening portion 10 without any difficulty.

In the above-described manner, the tip portion of the connection plug 11 is relatively fitted into the plug-receiving opening portion 10 of the body 2 and the first seal surface 12 which is the bottom surface of the plug-receiving opening portion 10 is relatively pressed by the tip face of the connection plug 11, whereby the first seal surface 12 is elastically deformed toward the base portion 8 of the body 2 and establishes liquid-tight contact with the tip face of the connection plug 11. In addition, the second seal surface 13 which is the side surface of the plug-receiving opening portion 10 is relatively pressed by the side surface of the tip portion of the connection plug 11, whereby second seal surface 13 is elastically deformed radially outwardly and establishes liquid-tight contact with the side surface of the tip portion of the connection plug 11. In this manner, the connecting coupler 1 is liquid-tightly connected to the connection plug 11 in a state of being pressed against the connection plug 11, thereby causing the solution transferring passage 9 of the body 2 and the interior of the connection plug 11 to communicate with each other.

Subsequently, when the pressure of the fixing mechanism 5 is released, the fixing mechanism 5 is returned to the fixing position shown in FIG. 1 by the coil spring 24, whereby the fixing mechanism 5 presses the balls 23 radially inwardly via the coil spring 24 and causes the balls 23 to move to the engagement position. Accordingly, the balls 23 disengageably engage with the peripheral groove 29 of the connection plug 11 so that the connecting coupler 1 and the connection plug 11 are fixed in the above-mentioned state.

Incidentally, when the connection between the connecting coupler 1 and the connection plug 11 is to be released, the fixing mechanism 5 is set to the release position and the connection plug 11 is relatively released from the connecting coupler 1, whereby the connection can be easily released.

According to the above-described construction example, the first seal surface 12 which is the bottom surface of the plug-receiving opening portion 10 is elastically deformed toward the base portion 8 of the body 2 by the tip face of the connection plug 11, whereby the first seal surface 12 is brought into liquid-tight contact with the tip face of the connection plug 11. In addition, the second seal surface 13, which is the side surface of the plug-receiving opening portion 10, is elastically deformed radially outwardly by the side surface of the tip portion of the connection plug 11, whereby the second seal surface 13 is brought into liquid-tight contact with the side surface of the tip portion of the connection plug 11. Accordingly, the connecting coupler 1 can be positively liquid-tightly connected to the connection plug 11.

In addition, since an O-ring or the like is not used, unlike the prior art, there is no problem that a dead space (gap) in which a dialysis solution stays is formed in a portion surrounding the O-ring, like the prior art. In addition, since the inside surface of the coupling portion 17 of the coupling tube 4 is made flush with and contiguous to the second seal surface 13, after the completion of dialysis, it is possible to easily perform cleaning of the portion of the inside surface of the coupling portion 17 or the like that is adjacent to the plug-receiving opening portion 10, not to mention the plug-receiving opening portion 10 of the body 2. Accordingly, there is no great risk that bacteria form in the connecting coupler 1, and there is also no great risk that a pyrogenic substance such as an endotoxin separated from bacteria enters into a dialysis solution.

In addition, in the connecting coupler 1, the coupling tube 4 and the fixing mechanism 5 for fixing the connection plug 11, as well as the line connector 3 to which a solution transferring line such as a dialysis solution circulating hose is connected, are not formed of an elastic material and are, therefore, large in strength. Accordingly, even if the connecting coupler 1 is used for a long term, there is no great risk that the coupling tube 4, the fixing mechanism 5 or the line connector 3 is deformed, nor a great risk that the connecting coupler 1 itself is deformed.

EFFECT OF THE INVENTION

As described hereinabove in detail, according to the invention, a connecting coupler can be positively liquid-tightly connected to a connection plug, and there is no great risk that bacteria form in the connecting coupler, and there is also no great risk that a pyrogenic substance such as an endotoxin separated from bacteria enters into a dialysis solution. In addition, even if the connecting coupler is used for a long term, there is no great risk that a coupling tube, a line connector or the like is deformed, nor a great risk that the connecting coupler itself is deformed.

In addition, according to the invention wherein the fixing mechanism is formed of a metal material, even if the connecting coupler is used for a long term, there is no great risk that the fixing mechanism is deformed, and the risk that the connecting coupler itself is deformed can be reduced to a further extent.

What is claimed is:

1. A dialyzer connecting coupler for connecting with a connection plug of a dialyzer, comprising:
    A) a body which is formed of an elastic material and has a solution transferring passage formed in its inside, the solution transferring passage having a plug-receiving opening portion opened at a tip portion of the solution transferring passage, a tip portion of the connection plug being adapted to be removably fitted into the plug-receiving opening portion;
    B) a line connector which is fitted into the body so that its inside communicates with the solution transferring passage, and to which a solution transferring line can be connected;
    C) a coupling tube which is formed in a tubular shape and has a fixing portion fixedly fitted on the tip portion of the body and a coupling portion projected from the fixing portion in an axial direction and that is adapted to be removably fitted onto a portion of the connection plug that excludes the tip portion of the plug; and
    D) a fixing mechanism which releasably fixes the coupling tube to the connection plug in a state of pressing the body against the connection plug,
    the plug-receiving opening portion being made larger in diameter than the portion of the solution transferring passage that neighbors the plug-receiving opening portion,
    an inside bottom of the plug-receiving opening portion forming a first seal surface which, when the connection plug is connected, is brought into abutment with the connection plug and is elastically deformed toward a base portion of the body to liquid-tightly contact with a tip face of the connection plug,
    a side surface of the plug-receiving opening portion forming a second seal surface which is made flush with and contiguous to an inside surface of the coupling portion of the coupling tube and, when the connection plug is connected, is brought into abutment with the connection plug and is elastically deformed diametrically outwardly to liquid-tightly contact with the side surface of the tip portion of the connection plug.

2. The dialyzer connecting coupler according to claim 1, wherein the fixing mechanism is formed of a metal material.

* * * * *